US012256935B2

(12) United States Patent
Tal

(10) Patent No.: US 12,256,935 B2
(45) Date of Patent: Mar. 25, 2025

(54) CONTROLLING RATE OF BLOOD FLOW TO RIGHT ATRIUM

(71) Applicant: VenaCore Inc., Tel-Aviv (IL)

(72) Inventor: Michael Gabriel Tal, Tel Aviv (IL)

(73) Assignee: VENACORE INC., Wilmington, DE (US)

( * ) Notice: Subject to any disclaimer, the term of this patent is extended or adjusted under 35 U.S.C. 154(b) by 1065 days.

(21) Appl. No.: 17/054,283

(22) PCT Filed: May 7, 2019

(86) PCT No.: PCT/US2019/031089
§ 371 (c)(1),
(2) Date: Nov. 10, 2020

(87) PCT Pub. No.: WO2019/221971
PCT Pub. Date: Nov. 21, 2019

(65) Prior Publication Data
US 2021/0177426 A1    Jun. 17, 2021

Related U.S. Application Data

(60) Provisional application No. 62/670,728, filed on May 12, 2018.

(51) Int. Cl.
*A61B 17/12* (2006.01)
*A61B 17/00* (2006.01)
*A61F 2/06* (2013.01)

(52) U.S. Cl.
CPC .. *A61B 17/12036* (2013.01); *A61B 17/12109* (2013.01); *A61B 17/12168* (2013.01);
(Continued)

(58) Field of Classification Search
CPC .................... A61F 2002/823; A61B 17/12036
See application file for complete search history.

(56) References Cited

U.S. PATENT DOCUMENTS 5,383,926 A    1/1995    Lock et al.
5,824,046 A    10/1998    Smith et al.
(Continued)

FOREIGN PATENT DOCUMENTS

WO    2017062740 A1    4/2017
WO    2018197983 A1    11/2018
(Continued)

*Primary Examiner* — Melanie R Tyson
*Assistant Examiner* — Yasniary De La Caridad Morales
(74) *Attorney, Agent, or Firm* — Veros Legal Solutions, LLP

(57) ABSTRACT

Blood flow affecting implant and implantation thereof in superior vena cava, optionally including disintegration of endothelium layer and inducing tissue ingrowth within implant. Implant includes elongated body with optional tubular inner layer forming orifice, shapeable to final orifice diameter for restricting blood flowing therethrough to chosen average flow rate; and/or tubular outer layer provided coaxially around inner layer. Outer layer is formed of second material provided in elastically deformable state for facilitating elastic radial self-expanding from collapsed diameter up to relaxed maximal expanded diameter greater than diameter of inner wall portion of superior vena cava. Inner layer is formed of first material, in plastically or elastically deformable state.

23 Claims, 10 Drawing Sheets

(52) U.S. Cl.
CPC .............. *A61B 17/12186* (2013.01); *A61B 2017/00862* (2013.01); *A61F 2002/068* (2013.01); *A61F 2230/001* (2013.01)

(56) References Cited

U.S. PATENT DOCUMENTS

| | | |
|---|---|---|
| 5,954,765 A | 9/1999 | Ruiz |
| 6,336,937 B1 | 1/2002 | Vonesh et al. |
| 6,350,277 B1 | 2/2002 | Kocur |
| 6,419,686 B1 | 7/2002 | McLeod et al. |
| 6,638,293 B1 | 10/2003 | Makower et al. |
| 6,878,160 B2 | 4/2005 | Gilligan et al. |
| 6,953,476 B1 | 10/2005 | Shalev |
| 7,159,593 B2 | 1/2007 | McCarthy et al. |
| 7,530,995 B2 | 5/2009 | Quijano et al. |
| 8,105,344 B2 | 1/2012 | Yeung et al. |
| 8,425,584 B2 | 4/2013 | Cully et al. |
| 8,556,954 B2 | 10/2013 | Muvhar et al. |
| 8,621,975 B2 | 1/2014 | Russo et al. |
| 8,858,612 B2 | 10/2014 | Ben-Muvhar et al. |
| 8,906,057 B2 | 12/2014 | Connor et al. |
| 8,911,489 B2 | 12/2014 | Ben-Muvhar |
| 8,923,973 B2 | 12/2014 | Gross |
| 9,107,743 B2 | 8/2015 | Iancea et al. |
| 9,364,354 B2 | 6/2016 | Ben-Muvhar et al. |
| 9,393,384 B1 * | 7/2016 | Kapur .............. A61B 17/12036 |
| 9,402,634 B2 | 8/2016 | Russo et al. |
| 9,681,876 B2 | 6/2017 | Cragg et al. |
| 9,707,124 B2 | 7/2017 | Brenzel et al. |
| 9,744,059 B2 | 8/2017 | Ben-Muvhar |
| 9,848,883 B2 | 12/2017 | Cragg et al. |
| 10,010,328 B2 | 7/2018 | Cragg et al. |
| 10,178,995 B2 | 1/2019 | Cragg et al. |
| 10,548,606 B2 | 2/2020 | Hui et al. |
| 2002/0045931 A1 | 4/2002 | Sogard et al. |
| 2003/0065386 A1 | 4/2003 | Weadock |
| 2004/0230288 A1 | 11/2004 | Rosenthal |
| 2005/0055082 A1 * | 3/2005 | Ben Muvhar .............. A61F 2/91 623/1.15 |
| 2005/0064009 A1 | 3/2005 | Bates |
| 2006/0106449 A1 | 5/2006 | Muvhar |
| 2006/0106450 A1 | 5/2006 | Muvhar |
| 2006/0116627 A1 | 6/2006 | Bridges et al. |
| 2011/0152998 A1 * | 6/2011 | Berez .............. A61F 2/95 623/1.15 |
| 2012/0316597 A1 | 12/2012 | Fitz et al. |
| 2014/0052103 A1 | 2/2014 | Cully et al. |
| 2014/0121759 A1 | 5/2014 | Cully |
| 2015/0173919 A1 | 6/2015 | Baldwin |
| 2015/0282958 A1 | 10/2015 | Centola et al. |
| 2016/0256169 A1 | 9/2016 | Ben-Muvhar et al. |
| 2017/0086854 A1 | 3/2017 | Cragg et al. |
| 2017/0165059 A1 | 6/2017 | Roselli et al. |
| 2017/0172771 A1 | 6/2017 | Bruckheimer et al. |
| 2018/0085128 A1 | 3/2018 | Bellomo et al. |
| 2018/0280167 A1 * | 10/2018 | Folan .............. A61F 2/90 |
| 2018/0303639 A1 | 10/2018 | Ben-Muvhar |
| 2019/0126014 A1 | 5/2019 | Kapur et al. |
| 2019/0133601 A1 | 5/2019 | Cragg et al. |
| 2019/0239998 A1 * | 8/2019 | Tuval .............. A61F 2/06 |
| 2019/0255302 A1 | 8/2019 | Kapur et al. |
| 2019/0307459 A1 * | 10/2019 | Celermajer .......... A61M 60/161 |
| 2019/0314551 A1 * | 10/2019 | Matheny .............. A61L 27/3834 |

FOREIGN PATENT DOCUMENTS

| | | |
|---|---|---|
| WO | 2018225059 A1 | 12/2018 |
| WO | 2019083989 A1 | 5/2019 |

\* cited by examiner

CONTROLLING RATE OF BLOOD FLOW TO RIGHT ATRIUM

FIELD OF THE INVENTION

The present invention, in some embodiments thereof, relates to methods and devices for treating heart failure conditions, and more particularly, but not exclusively, to treating congestive heart failure patients by way of controlling blood flow rate.

BACKGROUND OF THE INVENTION

Congestive heart failure (CHF) occurs when the heart is unable to maintain required blood flow throughout body vasculature or parts thereof, due to reduced heart muscles contractibility or relaxation, commonly following traumatic or continuous change to heart structure and/or the function. Failure of the left side of the heart causes blood to congest in the lungs, causing respiratory symptoms as well as fatigue due to insufficient supply of oxygenated blood. Failure of the right side of the heart is often caused by pulmonary heart disease, which is usually caused by difficulties of the pulmonary circulation, such as pulmonary hypertension or pulmonic stenosis.

SUMMARY OF THE INVENTION

The present invention relies on the assumption that reducing blood accumulation in the heart, while increasing blood volume particularly in the central veins, will assist cardiac function. In view thereof, the present invention, in some embodiments thereof, relates to methods and devices for treating heart failure conditions, and more particularly, but not exclusively, to treating congestive heart failure patients by way of controlling blood flow rate. By limiting flow in the superior vena cava (SVC) the risk of leg edema, deep vein thrombosis, renal and hepatic congestion and subsequent kidney and liver failure is reduced.

In an aspect of some embodiments of the present invention, there is provided a method for controlling rate of blood flow at entry to a right atrium via a superior vena cava, in a subject. The method includes at least one of the following steps (not necessarily in same order):

choosing a target location in the superior vena cava in proximity to the right atrium entry, the target location encloses a host lumen having an SVC cross-sectional area; and implanting a blood flow affecting implant at the target location, the implant comprises an orifice enclosing a constricted lumen having an orifice cross-sectional area, so as to reduce flow rate of blood from the superior vena to the right atrium flowable through the orifice;

In some embodiments, the orifice cross-sectional area is equal to or less than 50% of the SVC cross-sectional area.

In some embodiments, the orifice cross-sectional area is equal to or less than 25% of the SVC cross-sectional area.

In some embodiments, the orifice cross-sectional area is 50 mm$^2$ or less, optionally 20 mm$^2$ or less, optionally 10 mm$^2$ or less.

In some embodiments, the orifice is in a form of an adjustable orifice selectively changeable in shape, diameter or/and length, so as to affect flow rate of blood flowable through the orifice.

In some embodiments, the method further comprising:

measuring a pressure difference between a first measurement location in the superior vena cava, provided proximally adjacent to the target location, and a second measurement location in the right atrium; and if the measured pressure difference is out of a chosen pressure gradient range, adjusting the shape, diameter or/and length of the orifice, and repeating the measuring or/and adjusting until the measured pressure difference is within the chosen pressure gradient range.

In some embodiments, the chosen pressure gradient range has a minimal value of at least 2 mmHg.

In some embodiments, the chosen pressure gradient range is between 4 and 10 mmHg, optionally from 6 to 8 mmHg.

In some embodiments, the target location is distanced from the right atrium entry by not more than 100 mm, optionally by not more than 50 mm, optionally by not more than 10 mm.

In some embodiments, the implanting includes positioning the implant so as to extend between joining of an azygos vein with the superior vena cava and the right atrium entry.

In some embodiments, the implanting includes positioning the implant so as to extend across joining of an azygos vein or/and hemiazygos vein with the superior vena cava and the orifice is positioned between the joining of an azygos vein or/and hemiazygos vein with the superior vena cava and the right atrium entry.

In some embodiments, the implant includes a tubular outer surface sized and configured for fitting and laterally pressing against walls of the superior vena cava at the target location, and a tubular inner surface comprising the orifice.

In some embodiments, the implant inner surface has a gradually changing implant inner diameter along length of the implant, wherein the orifice merges with a minimal inner diameter of the inner surface.

In some embodiments, the implant inner surface in a form of a nozzle, optionally particularly a bell-shaped nozzle, having a nozzle throat which comprises the orifice.

In some embodiments, the method further comprising adjusting the shape, diameter or/and length of the orifice, by fixedly changing a shape of the implant inner surface such that the minimal inner diameter thereof increases or decreases.

In some embodiments, the method further comprising adjusting the shape, diameter or/and length of the orifice, by fixedly changing a position, a shape or/and a length of the nozzle throat.

In some embodiments, the implant includes an implant wall extending between the implant inner surface and the implant outer surface, wherein the adjusting includes deforming a functional wall portion provided about the orifice.

In some embodiments, the implant wall encapsulates a fluid sealable volume, and the implant includes a port extending across the implant wall into the fluid sealable volume, the port is selectively manipulatable for delivering a fluid into, or for withdraw the fluid from, the fluid sealable volume, for facilitating the deforming the functional wall portion.

In some embodiments, the functional wall portion is configured with reduced stiffness relative to other portions of the implant wall, such that the adjusting alters the orifice diameter at a greater extent relative to diameter of the implant inner surface at the other portions of the implant wall.

In some embodiments, the functional wall portion includes an embracing element stiffer than the implant wall surrounding the implant outer surface about the orifice, being fixedly sized or sizable in a smaller constricting diameter relative to original diameter of the implant wall prior to constriction by the embracing element, thereby forming the orifice.

In some embodiments, the implant wall if formed of a fluid permeable porous or meshed structure configured to induce gradual tissue ingrowth thereinside when stationed in the superior vena cava for at least 3 weeks, thereby occluding blood flowing therethrough such that most or all blood flowing in the superior vena cava is forced to flow through the orifice.

In some embodiments, the implant wall if formed of a fluid impermeable structure configured to occlude blood flowing therethrough such that most or all blood flowing in the superior vena cava is forced to flow through the orifice.

In some embodiments, the method further comprising occluding an azygos vein or/and a hemiazygos vein.

In some embodiments, the occluding includes fixating, inducing or/and trapping emboli within the azygos vein or/and hemiazygos vein.

In an aspect of some embodiments of the present invention, there is provided a blood flow affecting implant comprising:
  an elongated body extending along a longitudinal axis between an implant distal end, configured for positioning in a superior vena cava closer to an entry of a right atrium, and an implant proximal end, configured for positioning in the superior vena cava farther from the entry of the right atrium relative to the implant distal end;
  a tubular inner layer formed of a first material extending along the longitudinal axis and forming an orifice shapeable to a final orifice diameter for restricting blood flowing through the orifice to a chosen average flow rate; and
  a tubular outer layer provided coaxially around the inner layer and extending along the longitudinal axis, the outer layer forming a self-expandable sleeve configured for radially pressing against an inner wall portion of the superior vena cava in proximity to the entry to the right atrium for anchoring the implant thereto, the outer layer is formed of a second material provided in an elastically deformable state for facilitating elastic radial self-expanding of the outer layer from a collapsed diameter (optionally approximating the orifice diameter) up to a relaxed maximal expanded diameter greater than diameter of the inner wall portion.

In some embodiments, the orifice is balloon expandable with the first material provided in a plastically deformable state for facilitating selective radial changeability in diameter of the orifice between a plurality of fixed diameters.

In some embodiments, the orifice is self-expandable with the first material provided in an elastically deformable state for facilitating self-expansion from a predetermined initial orifice diameter to the final orifice diameter of the orifice.

In some embodiments, the final orifice diameter inherently derives from opening size of the outer layer when pressing against the inner wall portion of the superior vena cava.

In some embodiments, the outer layer comprises a mesh or a wire-structure comprising at least one wire made of the second material.

In some embodiments, the outer layer has peripheral slits or struts configured for facilitating selective radial expansion thereof.

In some embodiments, the inner layer has peripheral slits or struts configured for facilitating selective radial expansion thereof.

In some embodiments, the inner layer comprises a mesh or a wire-structure comprising at least one wire formed of the first material.

In some embodiments, the inner layer has at least one conical portion having a maximal cone diameter at the implant proximal end or the implant distal end.

In some embodiments, the collapsed diameter of the outer layer is within a range of 2 mm to 6 mm.

In some embodiments, the relaxed maximal expanded diameter is within a range of 20 mm to 40 mm.

In some embodiments, the final orifice diameter is within a range of 3 mm to 10 mm.

In some embodiments, the inner layer and the outer layer are interconnected to form the implant body, wherein the implant body includes a mesh or a wire-structure comprising at least one wire of a first type made of the first material and from at least one wire of a second type made of the second material.

In some embodiments, the inner layer and the outer layer are intertwined with the wire of the first type and/or the wire of the second type.

In some embodiments, the inner layer and the outer layer are formed separately before being interconnected.

In some embodiments, the implant further comprising at least one prong projecting from and/or across the outer layer and away from the inner layer, sized and configured to penetrate at least partially and/or disintegrate an endothelium layer of the superior vena cava, sufficiently for inducing local stenosis and/or tissue remodeling, when the outer layer is pressing against the inner wall portion of the superior vena cava.

In some embodiments, the inner layer and/or the outer layer are coated or impregnated with a fluid impermeable material and/or enclosing a fluid impermeable element therebetween.

In an aspect of some embodiments of the present invention, there is provided a method for controlling rate of blood flow to a right atrium via a superior vena cava, in a subject. The method includes at least one of the following steps (not necessarily in same order):
  delivering the blood flow affecting implant to a target location in the superior vena cava in proximity to the entry to the right atrium entry, wherein the outer layer is confined to the collapsed diameter;
  allowing the outer layer to self-expand radially and press against an inner wall portion of the superior vena cava at the target location;
  expanding the orifice to a chosen fixed orifice diameter corresponding to a chosen reduced flow rate of blood flowing at the target location towards the right atrium;
In some embodiments, the method further comprising:
  measuring a pressure difference between a first measurement location in the superior vena cava, provided proximally adjacent to the target location, and a second measurement location in the right atrium; and
  if the measured pressure difference is out of a chosen pressure gradient range, adjusting the orifice diameter, and repeating the measuring or/and adjusting until the measured pressure difference is within the chosen pressure gradient range.

In some embodiments, the chosen pressure gradient range is between 4 and 10 mmHg, optionally from 6 to 8 mmHg.

In some embodiments, the target location is distanced from the right atrium entry by not more than 100 mm, optionally by not more than 50 mm, optionally by not more than 10 mm.

In an aspect of some embodiments of the present invention, there is provided a method for controlling rate of blood flow at entry to a right atrium via a superior vena cava, in a subject. The method includes at least one of the following steps (not necessarily in same order):

providing the blood flow affecting implant connected to an implant delivery apparatus comprising a delivery apparatus outer sleeve and a radially expandable delivery apparatus inner member, the delivery apparatus outer sleeve is sized with a sleeve inner diameter for confining the outer layer in the collapsed diameter, the delivery apparatus inner member extending in the inner layer along the longitudinal axis and across the orifice;

delivering the blood flow affecting implant with the delivery apparatus to a target location in the superior vena cava in proximity to the entry to the right atrium entry;

by way of operating the delivery apparatus:
withdrawing the delivery apparatus outer sleeve from the outer layer while maintaining the delivery apparatus inner member fixedly positioned, thereby allowing the outer layer to self-expand radially and to press against an inner wall portion of the superior vena cava at the target location;

expanding the delivery apparatus inner member to affect radial expansion of the orifice to a chosen fixed orifice diameter corresponding to a chosen reduced flow rate of blood flowing at the target location towards the right atrium;

collapsing the delivery apparatus inner member to disengage from the inner layer; and withdrawing the delivery apparatus away from the implant.

In some embodiments, the delivery apparatus inner member includes a balloon selectively inflatable to different diameters applicable for affecting changing of the orifice diameter within a predetermined range of fixed orifice diameters.

In some embodiments, withdrawing the delivery apparatus outer sleeve from the outer layer is followed by maneuvering the outer layer against the superior vena cava, thereby causing local disintegrating an endothelium layer of the superior vena cava.

In an aspect of some embodiments of the present invention, there is provided a method for affecting rate of blood flow entering a right atrium in a heart of a subject, the method comprising:

disintegrating an endothelium layer in a chosen target wall portion of a superior vena cava opened to the right atrium;

anchoring a blood flow affecting implant to the target wall portion, the implant comprising a tubular implant body having an implant proximal portion, an implant distal portion, and an implant intermediate portion provided between the implant proximal and distal portions, the implant intermediate portion is shaped with a narrowing and comprises a plurality of openings for allowing blood flow passage across the narrowing; and inducing stenosis and/or tissue remodeling of the superior vena cava at the target wall portion, sufficiently for gradually occupying a space formed between the narrowing and the target wall tissue with naturally occurring tissue ingrowth until effecting blocking of the blood flow from passing across the narrowing.

In some embodiments, the anchoring results with the narrowing being shaped to surround an orifice having a final orifice diameter configured for restricting blood flowing through the orifice to a chosen average flow rate, when the space is filled with the tissue ingrowth sufficiently to block the blood flow from passing across the narrowing.

In some embodiments, the anchoring results with the narrowing being shaped to cover entire cross section of a superior vena cava lumen occupied by the implant body, thereby completely blocking blood flow through the implant intermediate portion when the space is filled with the tissue ingrowth sufficiently to block the blood flow from passing across the narrowing.

In some embodiments, the proximal implant portion descends in diameter in a proximal-to-distal direction and/or the distal implant portion ascends in diameter in a proximal-to-distal direction.

In some embodiments, wherein the implant body includes a tubular inner layer forming the narrowing, and a tubular outer layer provided coaxially around the inner layer and configured for anchoring the implant to the target wall portion.

In some embodiments, the inner layer is formed of a first material provided in a plastically deformable state for facilitating selective radial changeability in diameter of the narrowing between a plurality of fixed diameters.

In some embodiments, the inner material is formed of a first material provided in an elastically deformable state for facilitating self-expansion from a predetermined initial orifice diameter to the final orifice diameter of the orifice.

In some embodiments, the inner layer and/or the outer layer includes a mesh, a wire, peripheral slits or struts.

In some embodiments, the disintegrating includes at least one of cutting, removing, trimming, heating and puncturing.

In some embodiments, the inducing includes the disintegrating and/or providing a tissue growth inducing agent such as growth factors in or around the space.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings.

DESCRIPTION OF SPECIFIC EMBODIMENTS OF THE INVENTION

The present invention, in some embodiments thereof, relates to methods and devices for treating heart failure conditions, and more particularly, but not exclusively, to treating congestive heart failure patients by way of controlling blood flow rate, optionally particularly into a heart's right atrium.

Figure 1:
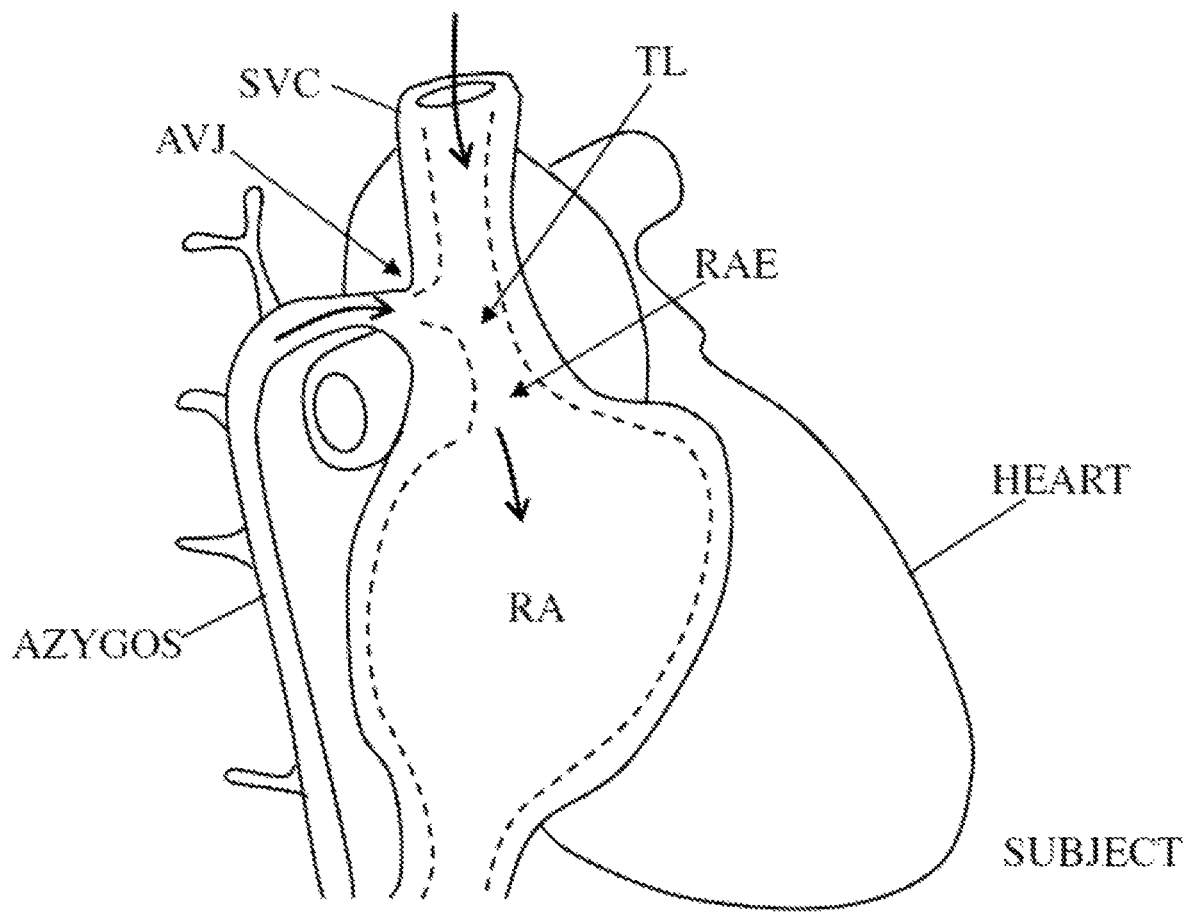
FIG. 1 schematically illustrates an uninterrupted blood flow via super vena cava and azygos vein into the right atrium in a subject's heart.

FIG. 1 schematically illustrates an uninterrupted blood flow via superior vena cava SVC and azygos vein AZYGOS into the right atrium RA in a subject's heart (SUBJECT, HEART). The SVC returns deoxygenated blood from the upper half of the body to the right atrium RA. The azygos vein AZYGOS transports deoxygenated blood from the posterior walls of the thorax and abdomen into the SVC; it also connects the systems of SVC and inferior vena cava and can provide an alternative path for blood to the RA when either of the venae cavae is blocked.

Figure 2:
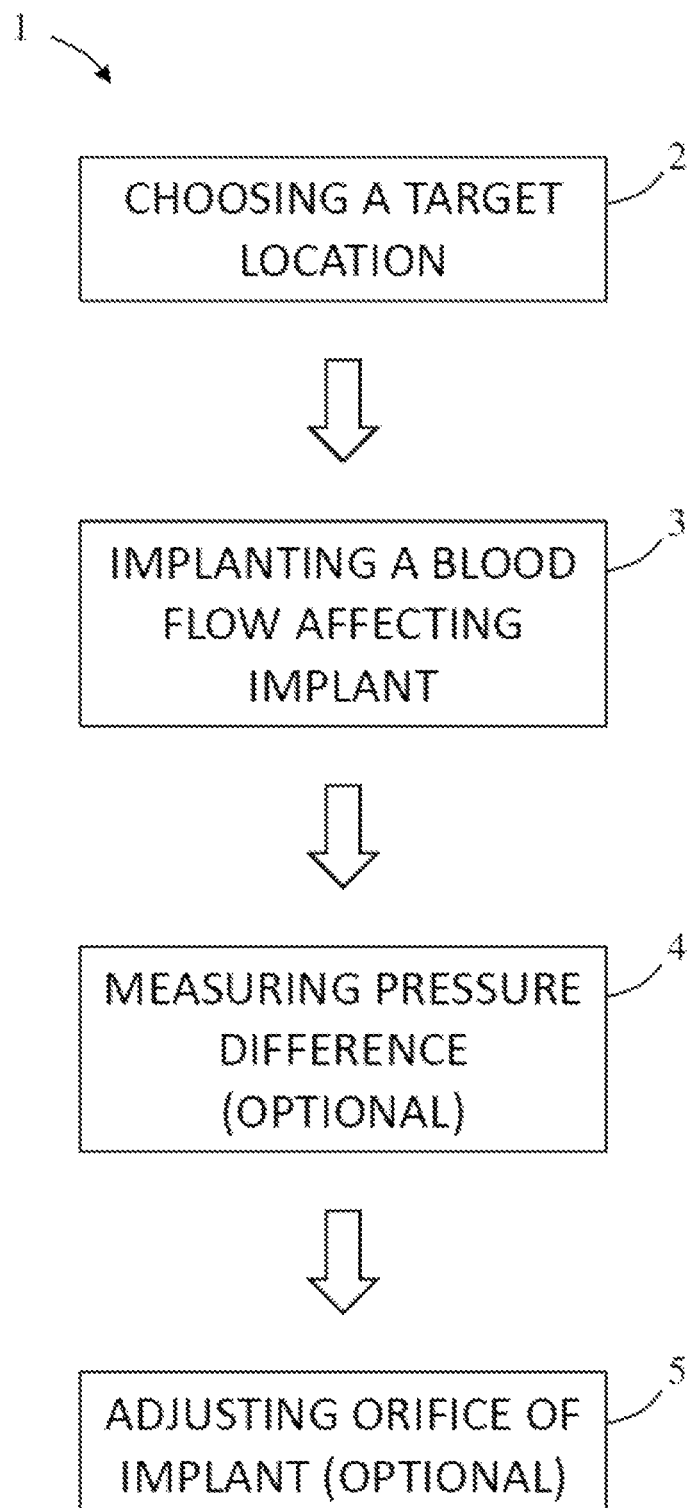
FIG. 2 shows flow chart representing steps in an exemplary method for controlling rate of blood flow at entry to a right atrium via a superior vena cava, in a subject, according to some embodiments of the invention.

The present invention provides a method 1, as shown in FIG. 2, for controlling rate of blood flow at an entry RAE to right atrium RA via the SVC, thereby reducing possibility for excessive blood accumulation in heart of a subject suffering from CHF.

At first, a target location TL in the superior vena cava SVC is chosen 2, at a portion located in proximity to the right atrium entry RAE. Target location TL encloses a host lumen having an SVC cross-sectional area. Target location TL is optionally distanced from right atrium entry RAE by not more than 100 mm, optionally by not more than 50 mm, optionally by not more than 10 mm.

After choosing target location TL, a blood flow affecting implant is implanted 3 there. The implant includes an orifice enclosing a constricted lumen with an orifice cross-sectional area, so as to reduce flow rate of blood from the SVC to the right atrium RA flowable through the orifice. The diameter enclosed by SVC at target location TL (the SVC diameter) is commonly within a range of 16 mm to 24 mm. In some embodiments, ratio of between final (e.g., adjusted after implantation) orifice diameter and SVC diameter is 1:3 or smaller (i.e., final orifice diameter is about 33% or less SVC diameter), at target location TL, optionally 1:4 or smaller (i.e., final orifice diameter is 25% or less SVC diameter) at target location TL, or optionally 1:5 or smaller (i.e., final orifice diameter is 20% or less SVC diameter) at target location TL. The orifice cross-sectional area is optionally about 50 mm$^2$ or less, optionally about 20 mm$^2$ or less, optionally about 10 mm$^2$ or less.

The implant may have an orifice having a fixed diameter in view of a pre-calculated reduction of blood flow rate in the target location, or alternatively, the orifice may be adjustable in diameter—prior to, during or/and post implantation.

Optionally, following implantation 3, the medical practitioner measures 4 a pressure difference between a first measurement location 6 in the superior vena cava SVC, provided proximally adjacent to target location TL, and a second measurement location 7 in the RA.

If the measured pressure difference is out of a chosen pressure gradient range, the medical practitioner may then adjust 5 shape, diameter or/and length of the implant's orifice, and may repeat measuring 4 or/and adjusting 5 until measured pressure difference is within the chosen pressure gradient range. The chosen pressure gradient range may have a minimal value of at least 2 mmHg, optionally between 4 and 10 mmHg, or optionally particularly from 6 to 8 mmHg.

Figure 3:
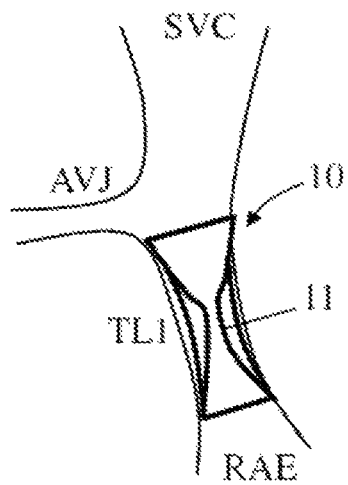
FIG. 3 schematically illustrates a cut view of a first target location in a superior vena cava portion equipped with a single orifice blood flow affecting implant, according to some embodiments of the invention.

FIG. 3 schematically illustrates a cut view of a first target location TL1 in superior vena cava SVC portion equipped with a blood flow affecting implant 10 having a single orifice 11. As shown, implanting 3 may include positioning implant 10 so as to extend between joining AVJ of azygos vein AZYGOS with superior vena cava SVC, and the right atrium entry RAE.

Figure 4:
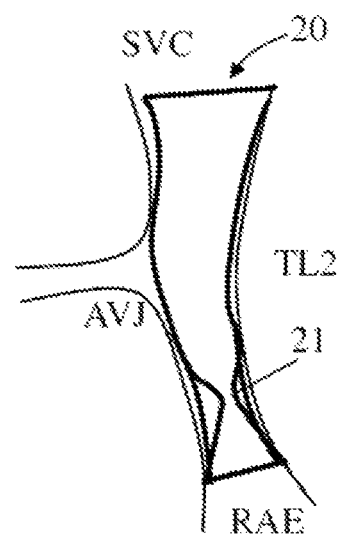
FIG. 4 schematically illustrates a cut view of a second target location in a superior vena cava portion equipped with a single orifice blood flow affecting implant, according to some embodiments of the invention.

FIG. 4 schematically illustrates a cut view of a second target location TL2 in superior vena cava SVC portion equipped with a blood flow affecting implant 20 having a single orifice 21. As shown, implanting 3 may include positioning implant 20 so as to extend across joining AVJ of azygos vein with superior vena cava SVC towards right atrium entry RAE. Optionally, orifice 21 is positioned between joining AVJ and right atrium entry RAE.

Figure 5:
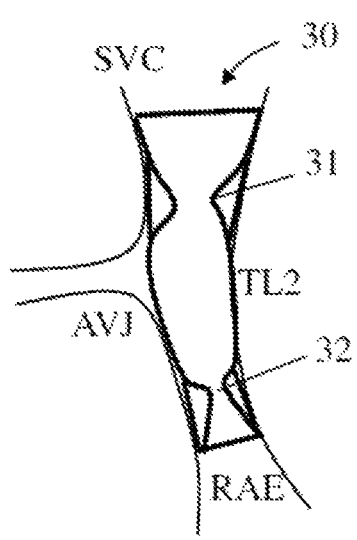
FIG. 5 schematically illustrates a cut view of a second target location in a superior vena cava portion equipped with a double-orifice blood flow affecting implant, according to some embodiments of the invention.

FIG. 5 schematically illustrates a cut view of second target location TL2 now equipped with a blood flow affecting implant 30 having two distinct orifices along length thereof: a first orifice 31 provided proximally to azygos vein joining AVJ, and a second orifice 32 provided between azygos vein joining AVJ and right atrium entry RAE. Having constrictions above and below azygos vein joining in SVC can reduce potential for retrograde flow back into azygos vein AZYGOS from SVC, while maintaining a requested total reduction in blood flow rate towards right atrium RA.

Figure 6A:
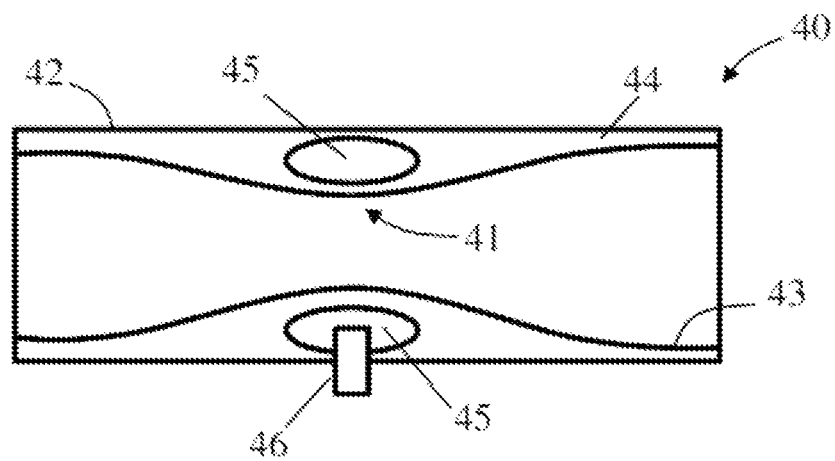
FIGS. 6A-6B schematically illustrate a cut view of a first type of blood flow affecting implant, according to some embodiments of the invention.
Figure 6B:
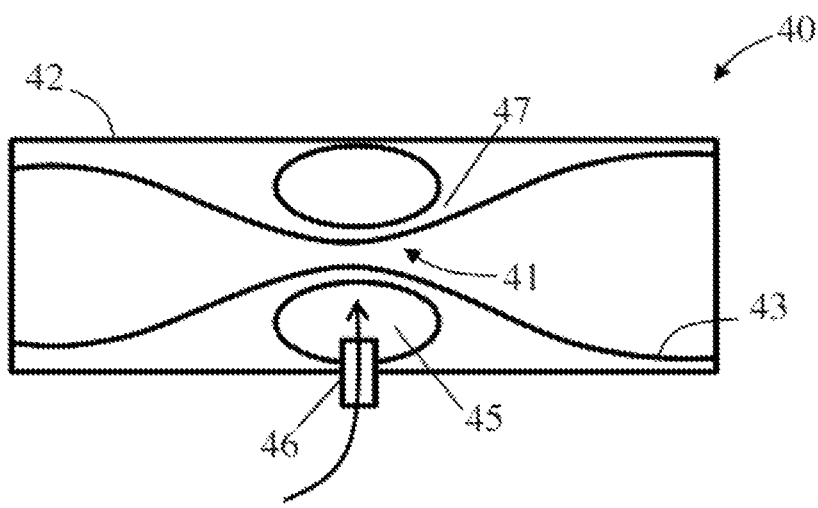

FIGS. 6A-6B schematically illustrate a cut view of a blood flow affecting implant 40 having an orifice 41 in a form of an adjustable orifice selectively changeable in shape, diameter and length, so as to affect flow rate of blood flowable therethrough. Implant 40 includes a tubular outer surface 42 sized and configured for fitting and laterally pressing against walls of the superior vena cava SVC at target location TL, and a tubular inner surface 43 forming orifice 41 at a portion thereof. Implant inner surface 43 has a gradually changing implant inner diameter along implant length, with orifice 41 merging with a minimal inner diameter of inner surface 43. Implant inner surface 43 is optionally in a form of a nozzle, optionally particularly a bell-shaped nozzle, having a nozzle throat which comprises orifice 41. Adjusting shape, diameter or/and length of orifice 41 may include fixedly changing a shape of implant inner surface 43 such that the minimal inner diameter thereof increases or decreases or/and by fixedly changing a position, a shape or/and a length of the nozzle throat.

Implant 40 includes an implant wall 44 extending between implant inner surface 43 and implant outer surface 42, and adjusting shape, diameter or/and length of orifice 41 also includes deforming a functional wall portion 47 provided about orifice 41. Implant wall 44 encapsulates a fluid sealable volume 45. Implant 40 includes a port 46 extending across implant wall 44 into fluid sealable volume 45. Port 46 is selectively manipulatable for delivering a fluid into (as shown in FIG. 6B), or for withdraw fluid from, fluid sealable volume 45 thereby deforming functional wall portion 47. Optionally, functional wall portion 47 is configured with reduced stiffness relative to other portions of implant wall 44, such that the adjusting alters orifice 41 diameter at a greater extent relative to diameter of implant inner surface 43 at other portions of implant wall 44.

Figure 7:
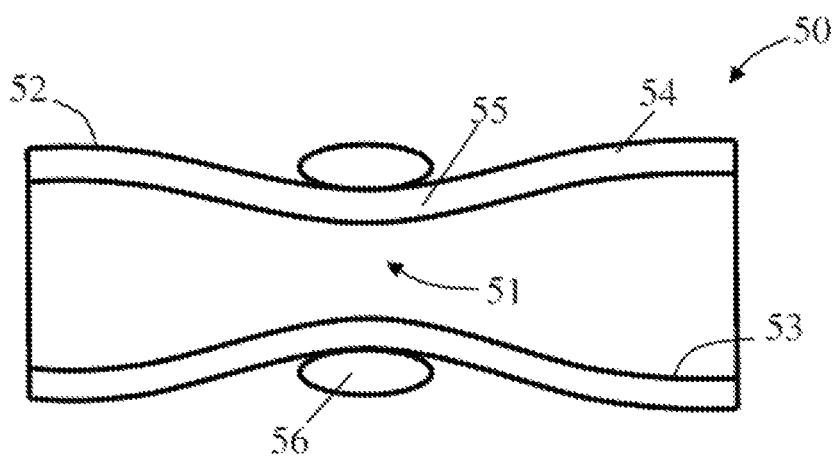
FIG. 7 schematically illustrates a cut view of a second type of blood flow affecting implant, according to some embodiments of the invention.

FIG. 7 schematically illustrates a cut view of another blood flow affecting implant 50 having a tubular outer surface 52 sized and configured for fitting and laterally pressing against walls of the superior vena cava SVC at target location TL, and a tubular inner surface 53 comprising an orifice 51. An implant wall 54 extending between implant inner surface 53 and implant outer surface 52, and adjusting shape, diameter or/and length of orifice 51 also includes deforming a functional wall portion 55 provided about orifice 51. Functional wall portion 55 includes an embracing element 56 stiffer than implant wall 54, being fixedly sized or sizable in a smaller constricting diameter relative to original diameter of implant wall 54 prior to constriction by embracing element 56, thereby forming orifice 51.

Figure 8A:
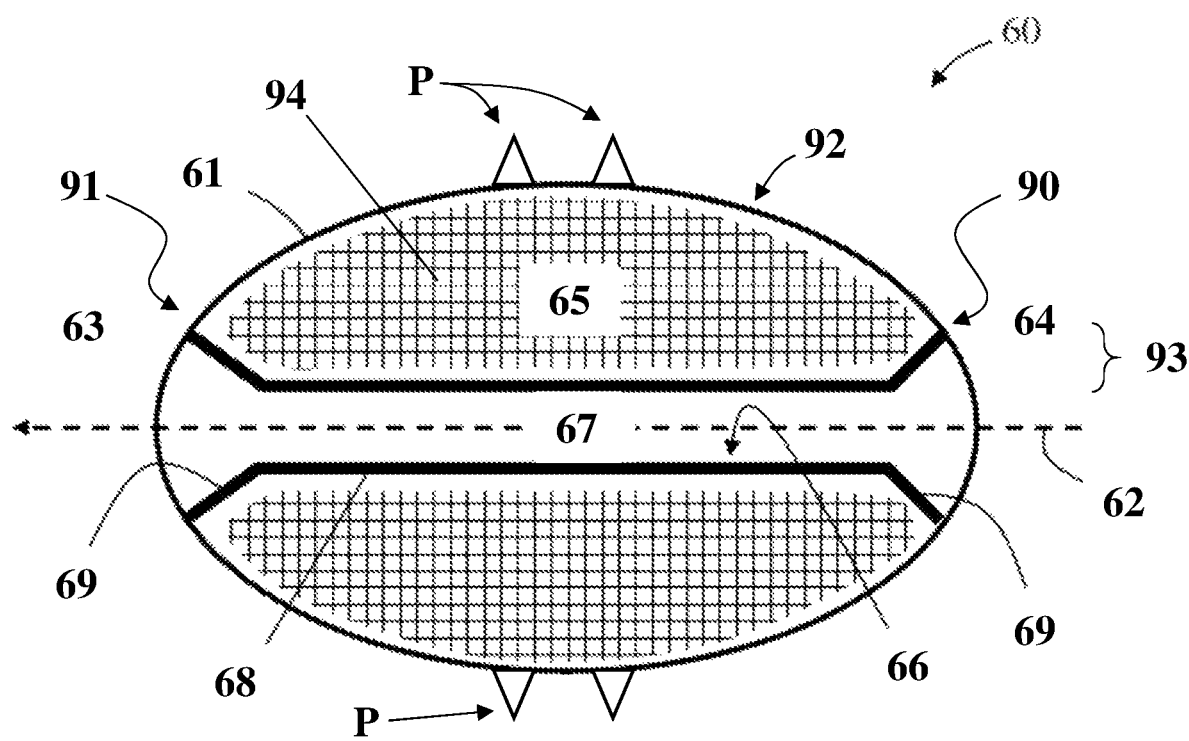
FIG. 8A schematically illustrates an exemplary blood flow affecting implant comprising an outer self-expandable layer and an inner balloon-expandable layer, according to some embodiments of the invention.

Reference is now made to FIG. 8A which schematically illustrates blood flow affecting implant 60 which may be an exemplary variation of implant 10. Implant 60 includes a tubular elongated implant body 61 extending along a longitudinal axis 62 between an implant distal end 63 and an implant proximal end 64. Implant distal end 63 is configured for positioning in a superior vena cava closer to an entry of a right atrium, and an implant proximal end 64 is configured for positioning in the superior vena cava farther from the entry of right atrium, relative to implant distal end 63.

Implant body 61 has an implant proximal portion 90, an implant distal portion 91, and an implant intermediate portion 92 provided between implant proximal and distal portions 90 and 91. Implant intermediate portion 92 is shaped with a narrowing 93 and comprises a plurality of openings 94 for allowing blood flow passage across narrowing 93. Proximal implant portion 90 descends in diameter and distal implant portion 91 ascends in diameter, in a proximal-to-distal direction. Implant body 61 includes a tubular inner layer 66 forming narrowing 93, and a tubular outer layer 65 provided coaxially around inner layer 66 and configured for anchoring implant 60 to a target wall portion.

Outer layer 65 and inner layer 66 are optionally formed as separate elements and then interconnected into forming implant body 61, and optionally differ in structure, in function and/or in material type and/or material processing. Outer layer 65 is optionally elastic and self-expandable and inner layer 66 may be provided either as a radially plastic structure (i.e., can be radially plastically deformable by compression or expansion to a chosen fixed diameter within a range of fixed diameters) or as a radially elastic structure (i.e., can be radially elastically deformable by compression or expansion from a singular relaxed form—indicated by minimal or no internal stresses—to a more stressed form, or vice versa). Optionally, at least one of inner layer 66 and outer layer 65 is formed as a stent having slits or struts, a mesh or a wire-structure, and/or includes at least one helically wound wire.

Inner layer 66 extends along longitudinal axis 62 and forms (e.g., enclose) an orifice 67 that is shapeable to a final orifice diameter for restricting blood flowing therethrough to a chosen average flow rate. Inner layer 66 is formed of a first material (optionally Ni—Ti alloy, Co—Cr alloy or an implant grade elastomer) that is optionally provided in a plastically deformable state for facilitating fixed radial changeability in an orifice diameter of orifice 67 within a predetermined range of orifice diameters, from an initial orifice diameter to a final orifice diameter. Although many materials or components can go through plastic deformation when stretched over yield point, the meaning of "plastically deformable state" in this disclosure refers to the physical state of such materials or components as provided in a finalized form as part of the implant 60, in a chosen prior to use condition.

Outer layer 65 also extends along longitudinal axis 62 and forms a self-expandable structure (e.g., in a form or function of a cage) configured for radially pressing against an inner wall portion of superior vena cava in proximity to the entry to right atrium for anchoring the implant thereto. Outer layer 65 includes a plurality of openings (e.g., fenestrated, meshed, cut slitted, or otherwise) sized and patterned to induce tissue ingrowth therethrough. At least one prong P projects from and/or across outer layer 65 and away from said inner layer 66, sized and configured to penetrate at least partially an endothelium layer of the superior vena cava, sufficiently for inducing stenosis and/or tissue remodeling adjacent the penetrated endothelium layer, when said outer layer is pressing against said inner wall portion of said superior vena cava. Outer layer 65 is formed of a second material (optionally Ni—Ti alloy, Co—Cr alloy or an implant grade elastomer) provided in an elastically deformable state for facilitating elastic radial self-expanding of outer layer 65 from a collapsed diameter approximating initial orifice diameter up to a relaxed maximal expanded diameter greater than diameter of the inner wall portion. Likewise, "elastically deformable state" in this disclosure refers to the physical state of materials or components as provided in finalized form as part of the implant 60, in a chosen prior to use condition.

Outer layer 65 optionally includes at least one wire made of the second material configured for facilitating selective elastic radial expansion thereof. In some embodiments, inner layer 66 is configured to block blood flowing therethrough and may be coated or impregnated with fluid impermeable material. Optionally and alternatively, a ring (optionally made of PTFE or other flexible or/and elastic biocompatible material) can be provided around inner layer 66 having thickness sized to effectively restrict blood from flowing through most or all cross section closed between inner layer 66 and outer layer 65. In another example, an intermediate layer may be provided between outer layer 65 and inner layer 66 which is optionally braided or otherwise interwoven with denser windings or/and coated with fluid impermeable material (optionally PTFE, EPTFE, PU or PE).

Inner layer 66 comprises a tube 68 made of the first material, optionally metal such as stainless-steel alloy (e.g., NI—Ti alloy or Co—Cr alloy), or plastic. Tube 68 may be smooth or seamless, or alternatively have structurally effecting wrinkles, openings or cuts (such as peripheral slits or mesh openings) configured for facilitating selective plastic radial expansion thereof. Tube 68 may comprise, for example, a mesh braided with at least one wire formed of the first material configured for facilitating selective plastic radial expansion thereof. Tube 68 conical portions 69 having a maximal cone diameter at both proximal end 64 and distal end 63 of implant 60.

The collapsed diameter of outer layer 65 is optionally within a range of 2 mm to 6 mm, optionally about 3 mm, and the relaxed maximal expanded diameter may be within a range of 20 mm to 40 mm, optionally about 30 mm. The initial orifice diameter is optionally within a range of about 1 mm to about 3 mm. The final orifice diameter is optionally within a range of about 3 mm to about 10 mm.

Implant body 61 may include a mesh braided with at least one wire of a first type made of the first material and from at least one wire of a second type made of the second material, so as to form inner layer 66 and outer layer 65. Inner layer 66 and outer layer 65 may be formed together and intertwined with the wires of both types, or they may be connected one with the other after separate forming of each.

Figure 8B:
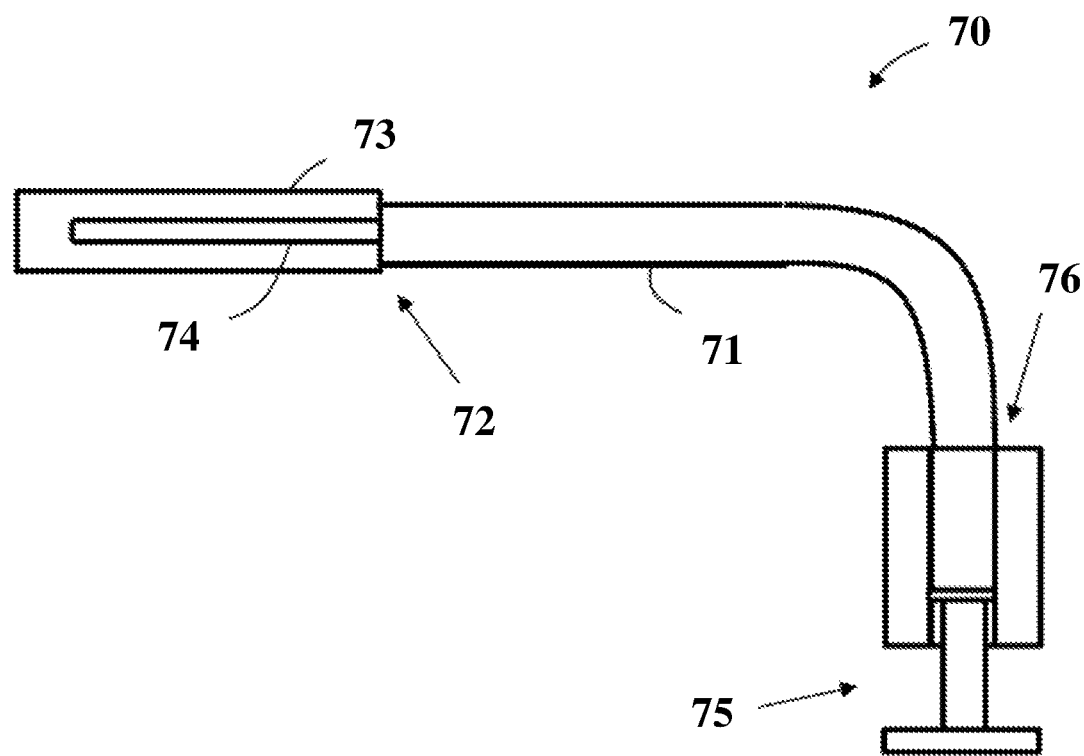
FIG. 8B schematically illustrates an exemplary apparatus for delivering and deploying the blood flow affecting implant shown in FIG. 8A, according to some embodiments of the invention.

FIG. 8B schematically illustrates an exemplary apparatus 70 for delivering and deploying blood flow affecting implant 60. Delivery apparatus 70 is in a form of a catheter and includes an elongated flexible lumenal body 71 connected at distal end 72 thereof to an outer sleeve 73 and to a radially expandable inner member 74. A syringe or pump 75 is connected at proximal end 76 of delivery apparatus 70 provided in fluid communication with inner volume of inner member 74, such that applying syringe 75 to pressurize fluid will affect delivery of the fluid via elongated body 71 into inner member 74, causing it to increase in size in accordance with pressure built up thereinside.

Outer sleeve 73 is sized with a sleeve inner diameter for confining outer layer 65 of implant 60 in its collapsed diameter. Inner member 74 is sized, when in a collapsed form, to reside within inner boundaries of inner layer 66, and configured for extending in inner layer 66 along longitudinal axis 62 and across orifice 67. Inner member 74 optionally includes or is in a form of a balloon that is selectively inflatable to different diameters applicable for affecting changing diameter of orifice 67 within a predetermined range of orifice diameters.

FIGS. 9A-9D schematically illustrate different scenarios representing exemplary steps in a method for delivering and deploying the blood flow affecting implant 60 using apparatus 70, for controlling rate of blood flow at entry to a right atrium via a superior vena cava SVC in a subject. Blood flow affecting implant 60 is optionally provided to the user (e.g., a physician, such as an interventional cardiologist) connected to implant delivery apparatus 70, optionally after completion of optional preliminary steps, which may include connecting between implant 60 and apparatus 70 for example.

Figure 9A:
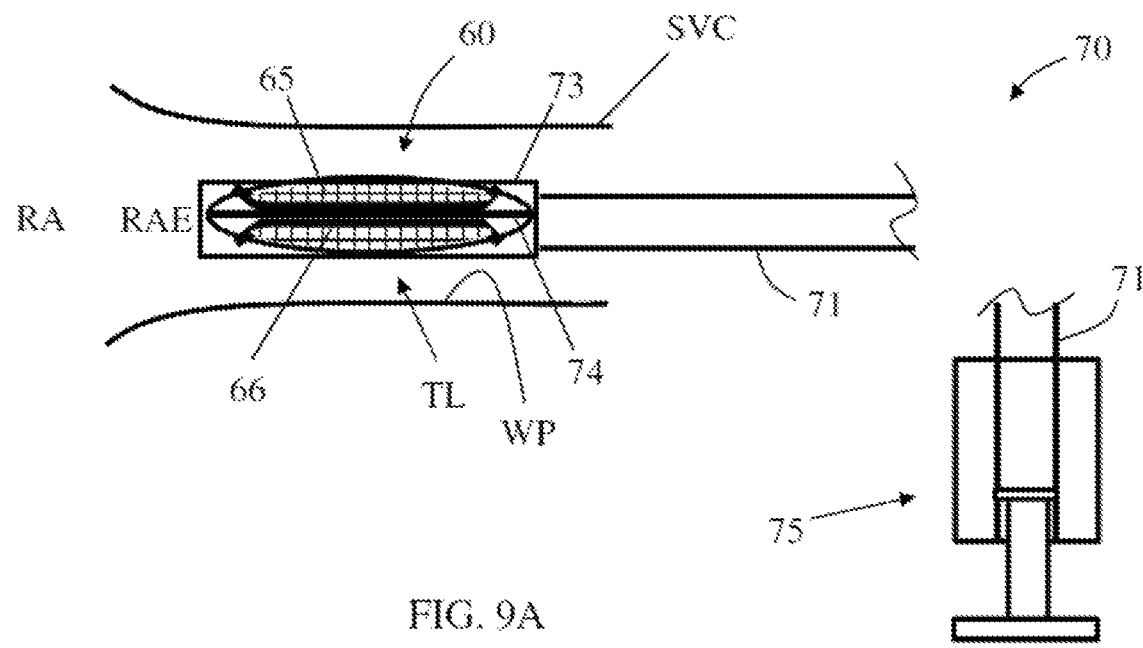
FIGS. 9A-9D schematically illustrate different scenarios representing exemplary steps in a method for delivering and deploying the blood flow affecting implant shown in FIG. 8A using the apparatus shown in FIG. 8B, according to some embodiments of the invention.

As shown in FIG. 9A, implant 60 is delivered with delivery apparatus 70 to a target location TL (e.g., target wall portion) in the superior vena cava SVC in proximity to the entry RAE to the right atrium entry RA. Target location TL is optionally distanced (optionally taken as a distance) from the right atrium entry RAE by not more than 100 mm, optionally by not more than 50 mm, optionally by not more than 10 mm.

Figure 9B:
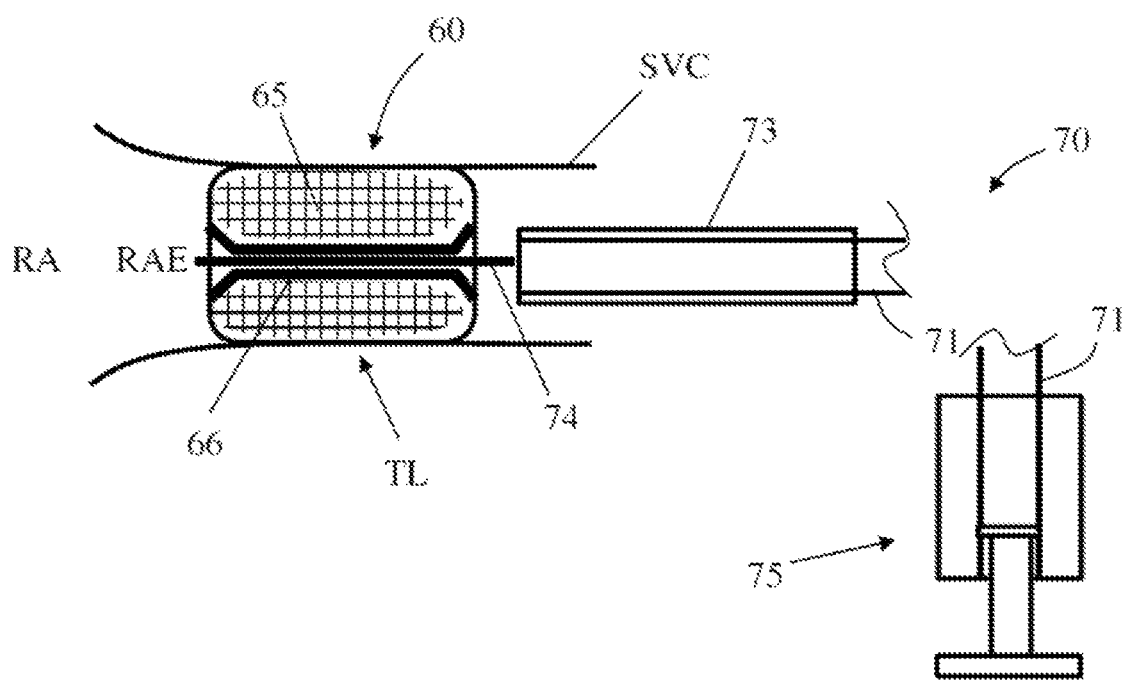

As shown in FIG. 9B, delivery apparatus 70 is operated for withdrawing outer sleeve 73 from outer layer 65 while maintaining inner member 74 fixedly positioned, thereby allowing outer layer 73 to self-expand radially and to press against an inner wall portion WP of superior vena cava SVC at target location TL. The delivery apparatus 70 may then be applied to rotate outer layer 73 against the superior vena cava, thereby causing local trauma to or loss of an endothelium layer of the superior vena cava. By locally damaging the endothelium layer, restenosis and/or tissue remodeling is induced, thereby potentially affecting natural generation of local thickening or narrowing of the superior vena cava.

Figure 9C:
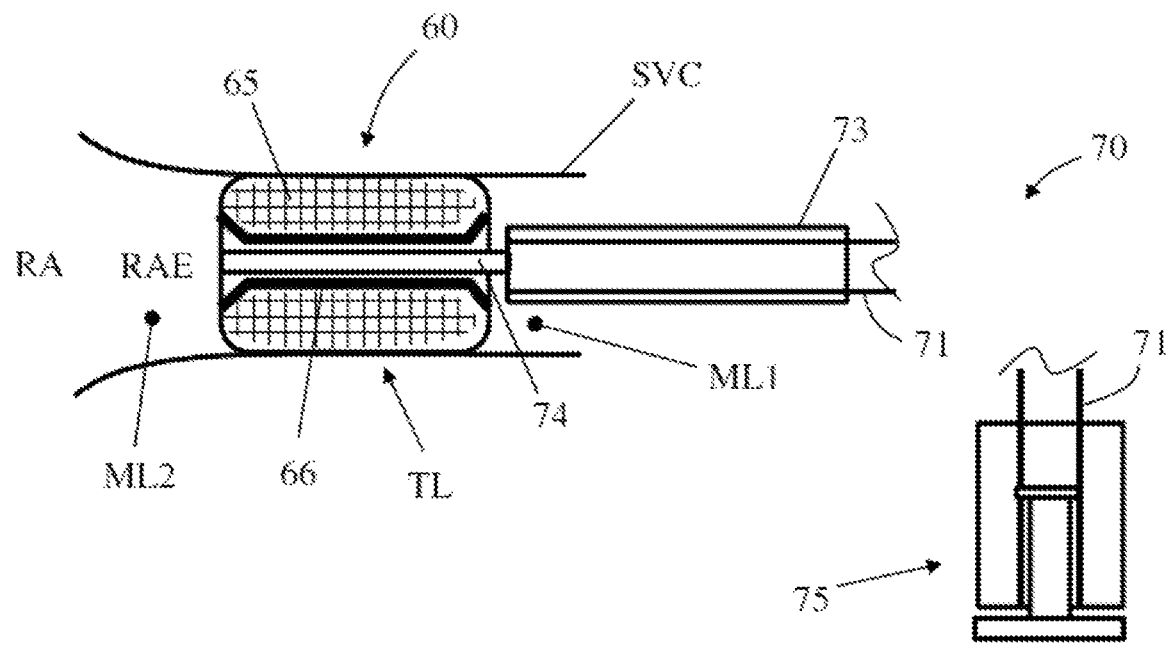

As shown in FIG. 9C, delivery apparatus 70 may then be operated for expanding inner member 74 to affect radial expansion of orifice 67 from a first fixed diameter to a second chosen fixed orifice diameter corresponding to a chosen reduced flow rate of blood flowing at target location TL towards the right atrium RA.

Pressure difference may be between a first measurement location ML1 in superior vena cava SVC, provided proximally adjacent to target location TL, and a second measurement location ML2 in right atrium RA (optionally at entry RAE thereto, or deeper inside right atrium RA), so that if the measured pressure difference is out of a chosen pressure gradient range (which is optionally between 4 and 10 mmHg, or optionally particularly from 6 to 8 mmHg), the orifice diameter may by adjusted (e.g., using apparatus 70 or otherwise), and measuring or/and adjusting may be repeated until said measured pressure difference is within the chosen pressure gradient range.

Figure 9D:
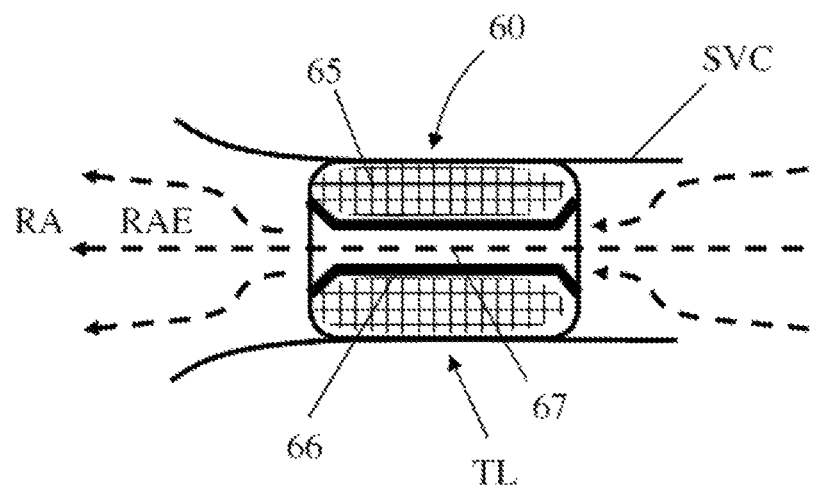

Once chosen flow rate and/or pressure gradient between implant proximal and distal ends 62 and 63 is met, inner member 74 can be collapsed to disengage from inner layer 66, and delivery apparatus 70 can be withdrawn away from implant 60 which can now function to affect blood flow into right atrium RA as chosen (FIG. 9D).

Optionally, means are implemented for inducing stenosis and/or tissue remodeling of the superior vena cava at target wall portion TL, sufficiently for gradually occupying a space formed between narrowing 93 and the surrounding wall tissue with naturally occurring tissue ingrowth, until effecting blocking of blood flow from passing across narrowing 93. Such means may include disintegration of an endothelium layer in target wall portion TL, and/or providing a tissue growth inducing agent such as growth factors in or around that space formed around narrowing 93. Endothelium layer disintegration can include tissue cutting, removing, trimming, heating and/or puncturing, optionally using prongs P or by using a separate device, for example.

Optionally, when the space around narrowing 93 is filled with tissue ingrowth sufficiently to block blood flow from passing across narrowing 93, blood is restricted to flow only through orifice 67. Alternatively, if narrowing 93 is shaped to cover entire cross section of a superior vena cava lumen occupied by implant body 61, when the space around narrowing 93 is filled with tissue ingrowth sufficiently to block blood flow from passing across narrowing 93, blood is completely blocked from flowing implant intermediate portion 92 and prevented from entering the right atrium via the superior vena cava.

Figure 10A:
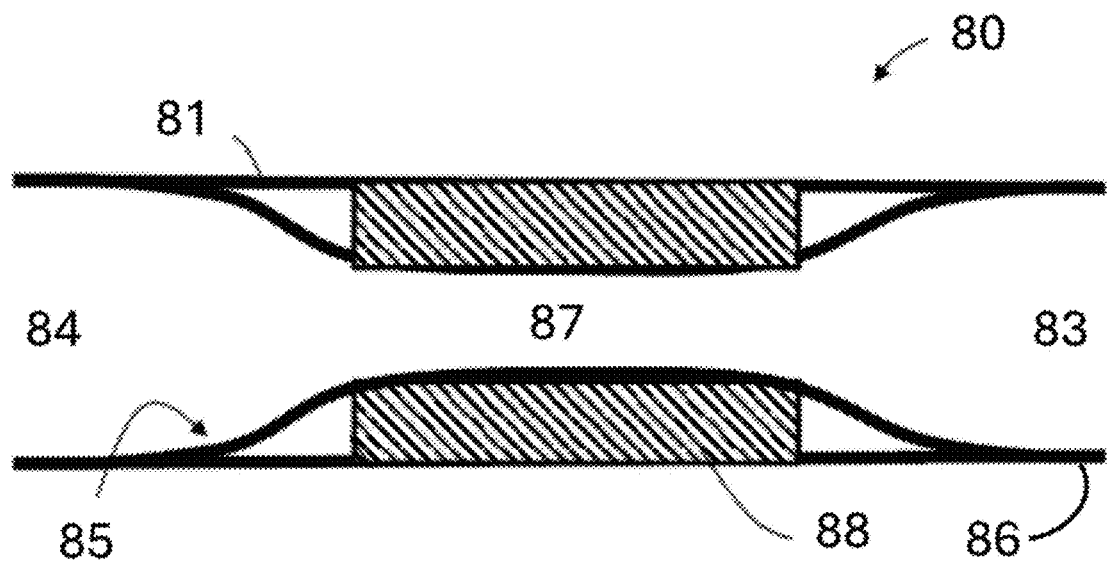
FIGS. 10A-10B schematically illustrate other exemplary blood flow affecting implants, according to some embodiments of the invention.

Reference is now made to FIG. 10A which schematically illustrates blood flow affecting implant 80 which may be another exemplary variation of implant 10. Implant 80 includes an elongated body 81 extending between an implant distal end 83 and an implant proximal end 84. Implant distal end 83 is configured for positioning in a superior vena cava closer to an entry of a right atrium, and an implant proximal end 84 is configured for positioning in the superior vena cava farther from the entry of right atrium, relative to implant distal end 83.

Implant 80 (and implant body 81) includes a tubular self-expandable inner layer 85 shaped as a convergent-divergent nozzle provided coaxially to a tubular plastically deformable outer layer 86. Inner layer 85 forms (e.g., constrict) a balloon expandable orifice 87 that is configured for restricting blood flowing therethrough to a chosen average flow rate. Outer layer 86 is formed of a first material (optionally Ni—Ti alloy, Co—Cr alloy or an implant grade elastomer) that is provided in a plastically deformable state for facilitating fixed radial changeability in an orifice diameter of orifice 87 within a predetermined range of orifice diameters.

Outer layer 86 may be smooth or seamless, or alternatively have structurally effecting wrinkles, openings or cuts (such as peripheral slits or mesh openings) configured for facilitating selective plastic radial expansion thereof. Outer layer 86 may comprise, for example, a mesh braided with at least one wire formed of the first material configured for facilitating selective plastic radial expansion thereof.

Inner layer 85 encompass a self-expandable structure 88 configured for expanding radially thereby forcing outer layer 86 into pressing against an inner wall portion of superior vena cava in proximity to the entry to right atrium for anchoring the implant thereto. Inner layer 85 is formed of a second material (optionally Ni—Ti alloy, Co—Cr alloy or an implant grade elastomer) provided in an elastically deformable state for facilitating elastic radial self-expanding of inner layer 85 from a collapsed diameter approximating orifice diameter up to a relaxed maximal expanded diameter greater than diameter of the inner wall portion. In some embodiments, inner layer 85 is formed of a fluid impermeable structure and is shaped so as to facilitate effective occluding to prevent or block blood from passing therethrough other than through orifice 87.

The collapsed diameter of outer layer 86 is optionally within a range of 2 mm to 6 mm, optionally about 3 mm, and the relaxed maximal expanded diameter may be within a range of 15 mm to 40 mm, optionally about 30 mm. The initial orifice diameter is optionally within a range of about 1 mm to about 3 mm. The final orifice diameter is optionally within a range of about 3 mm to about 10 mm.

Figure 10B:
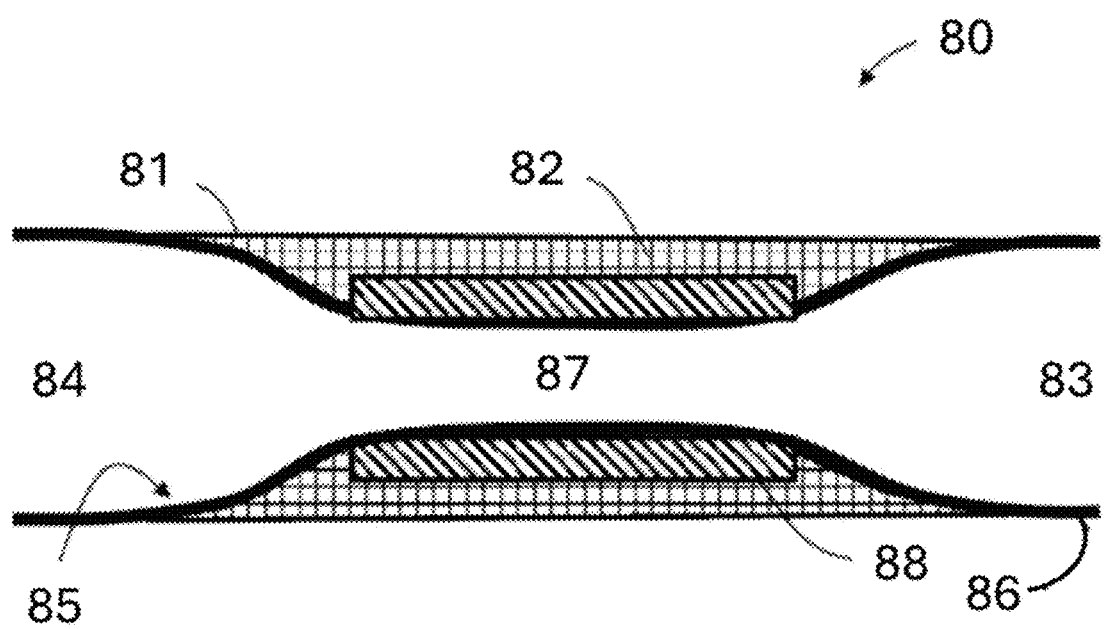

FIG. 10B shows a variation of implant 80 further comprising an intermediate layer 82 which is provided in a recess formed between structure 88 and around outer layer 86. Intermediate layer 82 is formed of a self-expandable mesh structure braided with at least one wire made of the second material configured for facilitating selective elastic radial expansion thereof.

Figure 11A:
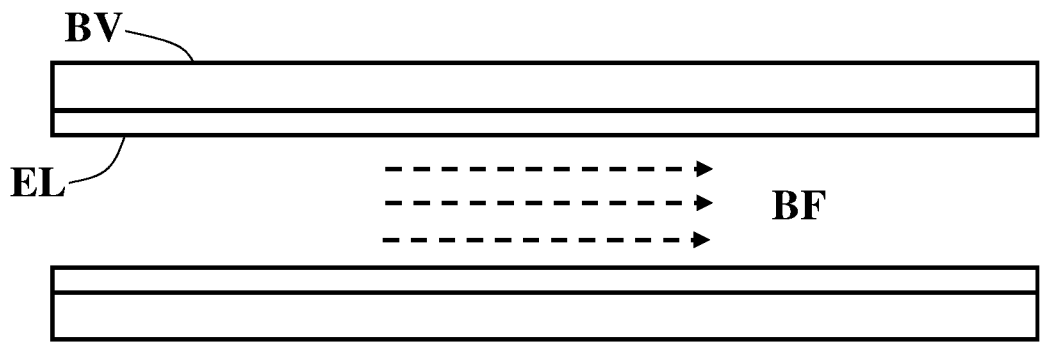
FIGS. 11A-11D schematically illustrate different scenarios representing exemplary steps in a method for reducing blood flow in a portion of a blood vessel, according to some embodiments of the invention.
Figure 11B:
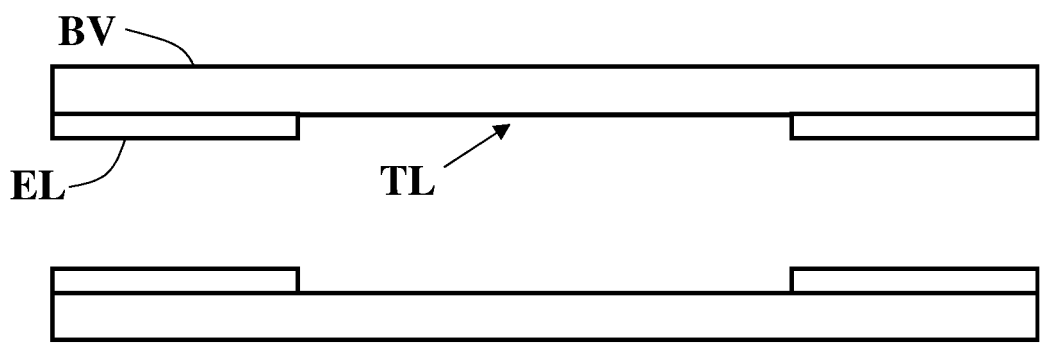
Figure 11C:
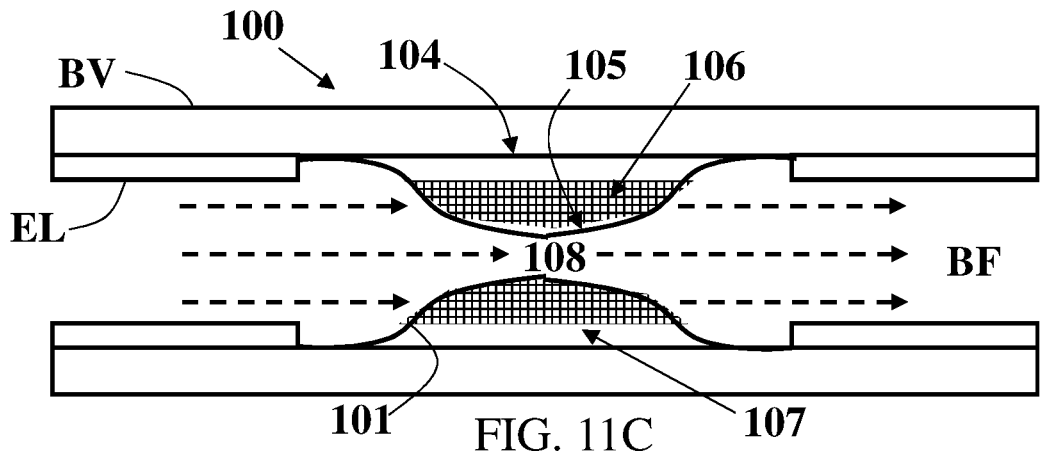
Figure 11D:
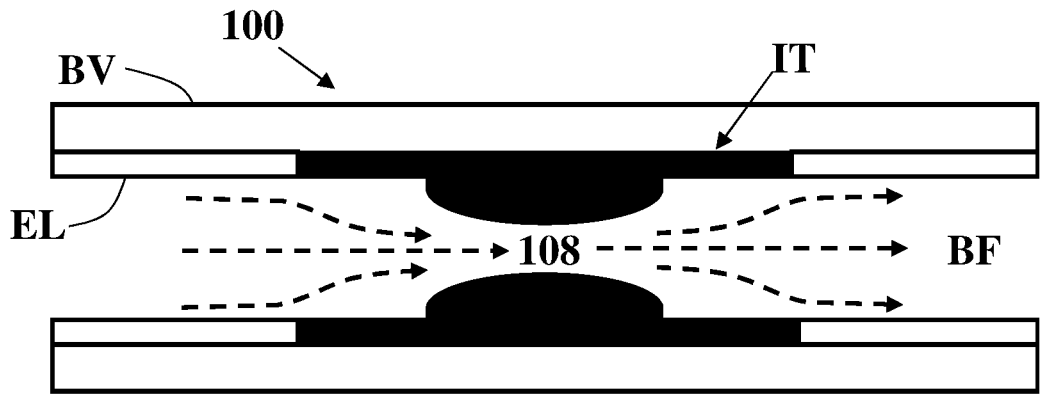

FIGS. 11A-11D schematically illustrate different scenarios representing exemplary steps in a method for reducing blood flow in a portion of a blood vessel BV. Blood vessel BV may be an artery or a vein, optionally a large vein such as the superior vena cava, such that the method can be applied for affecting rate of blood flow entering a right atrium in a heart of a subject. FIG. 11A shows blood vessel BV before procedure, with an intact endothelium layer EL and regular blood flow BF flowing in the blood vessel lumen. FIG. 11B schematically illustrates an exemplary outcome of an optional step of disintegrating endothelium layer EL in a chosen target wall portion TL of blood vessel BV. "Disintegrating" refers to any mechanical, chemical, biological or physical or other way to create a local physical damage or trauma to a chosen portion of endothelium layer EL fully or to thickness thereof, which may include one or any combination of cutting, removing, trimming, heating and/or puncturing endothelium layer EL and/or its adjacent surrounding tissue. The intention for performing this optional step can be to induce natural reaction of local stenosis and/or tissue remodeling, and/or to improve or facilitate matching and/or anchoring of a blood flow affecting implant 100 to target wall portion TL as shown in FIG. 11C.

Implant 100 may be an exemplary variation of either one of implants 10, 20, 30, 40, 50, 60 and 80, and is comprising of at least a tubular implant body 101 having an implant intermediate portion 104 provided between implant proximal and distal portions. Implant intermediate portion 104 is shaped with a narrowing 105 and comprises a plurality of openings 106 for allowing blood flow passage across narrowing 105. Anchoring implant 100 results with narrowing 105 shaped to surround an orifice 108 having a final orifice diameter, which can be for example between ½ to ¹⁄₁₀ of original diameter of blood vessel BV lumen enclosed by target wall tissue TL.

Instead of, as part of, or in addition to disintegrating endothelium layer EL, prior to or during anchoring of implant 100, other means can be applied for inducing stenosis and/or tissue remodeling of blood vessel BV at target wall portion TL, which advantageously be sufficient for naturally occurring tissue ingrowth IT to gradually occupy a space 107 formed between narrowing 105 and target wall tissue TL, until effectively preventing blood flow BF from passing across narrowing 105 (FIG. 11D) and restricting blood BF flowing only through orifice 108. Tissue growth inducing may include, for example, filling space 107, coating surfaces of implant 100 configured for contacting with blood vessel BV or otherwise providing a tissue growth inducing agent such as growth factors in or around space 107.

Figure 12A:
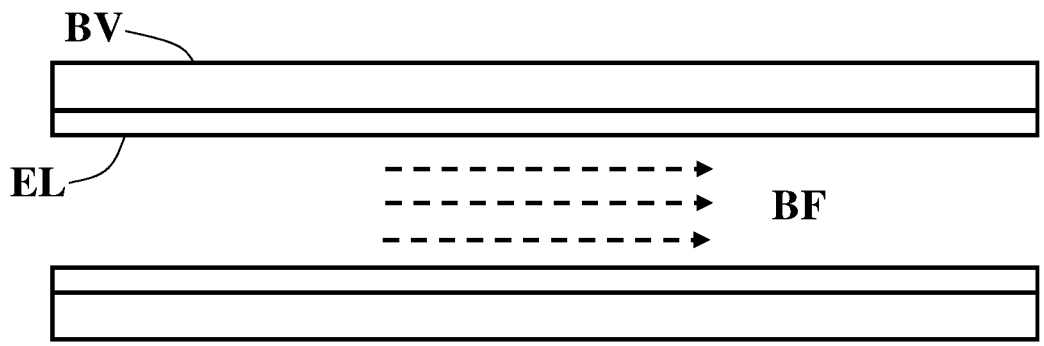
FIGS. 12A-12D schematically illustrate different scenarios representing exemplary steps in a method for occluding a blood vessel, according to some embodiments of the invention.
Figure 12B:
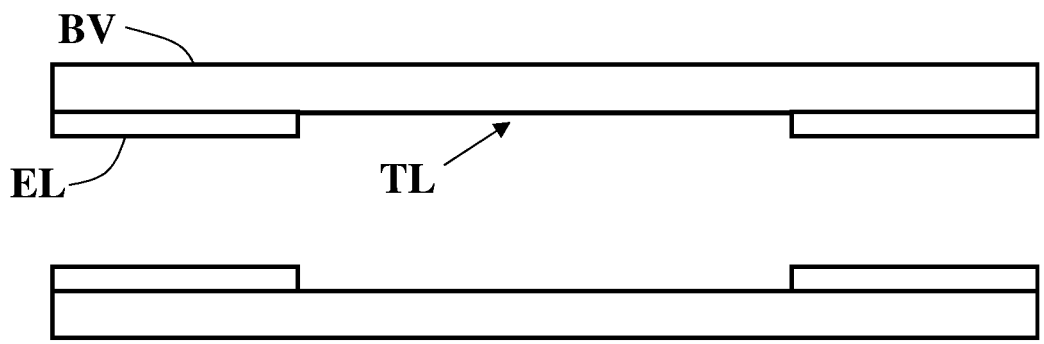

FIGS. 12A-12D schematically illustrate different scenarios representing exemplary steps in a method for occluding a blood vessel BV. Blood vessel BV may be an artery or a vein, optionally a large vein such as the superior vena cava, such that the method can be applied for affecting rate of blood flow entering a right atrium in a heart of a subject. FIG. 12A shows blood vessel BV before procedure, with an intact endothelium layer EL and regular blood flow BF flowing in the blood vessel lumen. FIG. 12B schematically illustrates an exemplary outcome of an optional step of disintegrating endothelium layer EL in a chosen target wall portion TL of blood vessel BV, as described above.

Figure 12C:
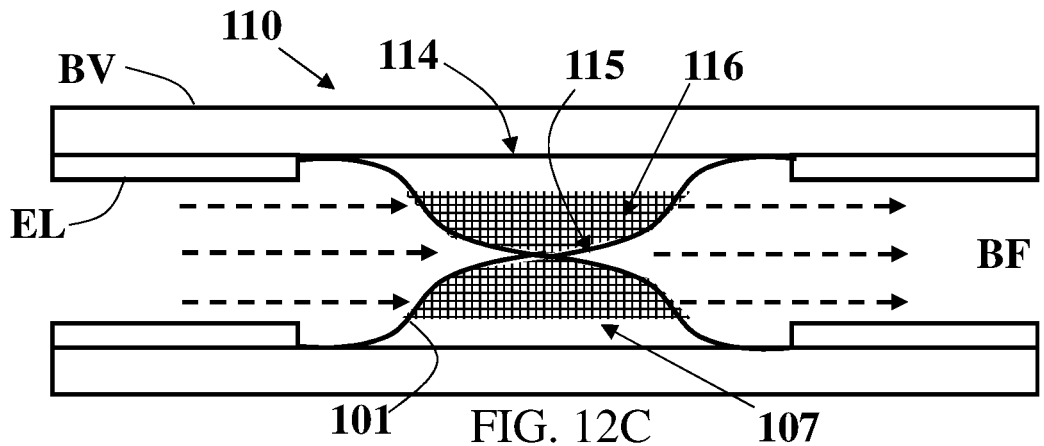

A blood flow affecting implant 110 is anchored to target wall portion TL as shown in FIG. 12C. Implant 110 may be an exemplary variation of either one of implants 10, 20, 30, 40, 50, 60, 80, and 100, and comprises of at least a tubular implant body 111 having an implant intermediate portion 114 provided between implant proximal and distal portions. Implant intermediate portion 114 is shaped with a narrowing 115 and comprises a plurality of openings 116 for allowing blood flow passage across narrowing 115. Anchoring implant 110 results with narrowing 115 shaped to cover entire cross section of a superior vena cava lumen occupied by implant body 111.

Figure 12D:
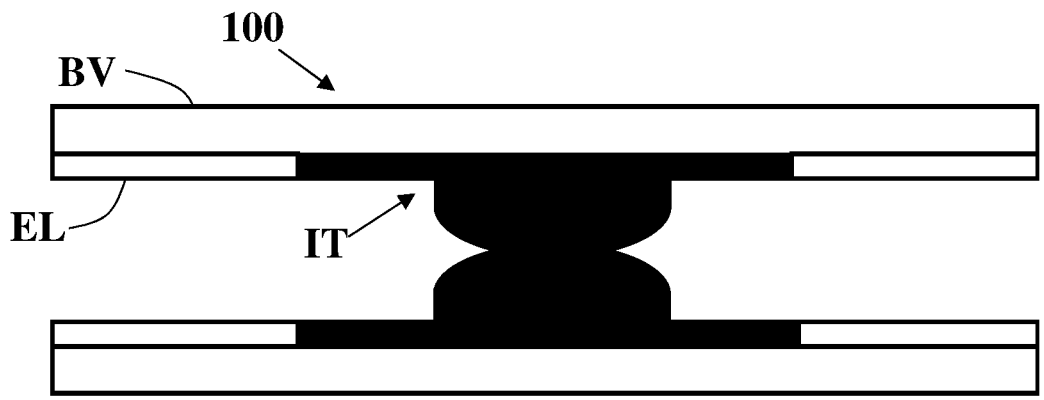

Instead of, as part of, or in addition to disintegrating endothelium layer EL, prior to or during anchoring of implant 110, other means can be applied for inducing stenosis and/or tissue remodeling of blood vessel BV at target wall portion TL, which advantageously be sufficient for naturally occurring tissue ingrowth IT to gradually occupy a space 117 formed between narrowing 115 and target wall tissue TL, until completely blocking blood flow BF from passing across narrowing 115 and through implant intermediate portion 114 (FIG. 12D). Tissue growth inducing may include, for example, filling space 117, coating surfaces of implant 110 configured for contacting with blood vessel BV or otherwise providing a tissue growth inducing agent such as growth factors in or around space 117.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A method for affecting rate of blood flow entering a right atrium in a heart of a subject, the method comprising:
    disintegrating an endothelium layer in a chosen target wall portion of a superior vena cava opened to the right atrium by removing and/or damaging some or all of the endothelium layer in the target wall portion of the superior vena cava;
    after the disintegrating, anchoring a blood flow affecting implant to said target wall portion, said implant comprising a tubular implant body having an implant proximal portion, an implant distal portion, and an implant intermediate portion provided between said implant proximal and distal portions, said implant intermediate portion is shaped with a narrowing and comprises a plurality of openings for allowing blood flow passage across said narrowing; and
    wherein the disintegrating is sufficient for inducing stenosis and/or tissue remodeling of the superior vena cava at said target wall portion, sufficiently for gradually occupying a space formed between said narrowing and said target wall portion with naturally occurring tissue ingrowth until effecting blocking of said blood flow from passing across said narrowing.

2. The method according to claim 1, wherein said anchoring results with said narrowing being shaped to surround an orifice having a final orifice diameter configured for restricting blood flowing through said orifice to a chosen average flow rate, when said space is filled with said tissue ingrowth sufficiently to block said blood flow from passing across said narrowing.

3. The method according to claim 1, wherein said anchoring results with said narrowing being shaped to cover an entire cross section of a superior vena cava lumen occupied by said implant body, thereby completely blocking blood flow through said implant intermediate portion when said space is filled with said tissue ingrowth sufficiently to block said blood flow from passing across said narrowing.

4. The method according to claim 1, wherein said proximal implant portion descends in diameter in a proximal-to-distal direction and/or said distal implant portion ascends in diameter in a proximal-to-distal direction.

5. The method according to claim 1, wherein said implant body includes a tubular inner layer forming said narrowing, and a tubular outer layer provided coaxially around said inner layer and configured for anchoring the implant to said target wall portion.

6. The method according to claim 5, wherein said inner layer is formed of a first material provided in a plastically deformable state for facilitating selective radial changeability in diameter of said narrowing between a plurality of fixed diameters.

7. The method according to claim 5, wherein said inner layer is formed of a first material provided in an elastically deformable state for facilitating self-expansion from a predetermined initial orifice diameter to said final orifice diameter of said orifice.

8. The method according to claim 5, wherein said inner layer and/or said outer layer includes a mesh, a wire, peripheral slits or struts.

9. The method according to claim 5, wherein the disintegrating is performed by rotating the outer layer against the blood vessel.

10. The method according to claim 1, wherein said inducing further comprises providing a tissue growth inducing agent in or around said space.

11. The method according to claim 10, wherein said tissue growth inducing agent comprises growth factors.

12. A method comprising:
    disintegrating an endothelium layer in a chosen target wall portion of a blood vessel by removing and/or damaging some or all of the endothelium layer in the target wall portion of the blood vessel;
    after the disintegrating, anchoring a blood flow affecting implant to said target wall portion, said blood flow affecting implant comprising an implant body having a narrowing and a plurality of openings for allowing blood flow passage across said narrowing; and
    wherein the disintegrating is sufficient for inducing stenosis and/or tissue remodeling of the blood vessel at said target wall portion, sufficiently for gradually occupying a space formed between said narrowing and said target wall tissue with naturally occurring tissue ingrowth until effecting blocking of said blood flow from passing across said narrowing.

13. The method according to claim 12, wherein said anchoring results with said narrowing being shaped to surround an orifice having a final orifice diameter configured for restricting blood flowing through said orifice to a chosen average flow rate, when said space is filled with said tissue ingrowth sufficiently to block said blood flow from passing across said narrowing.

14. The method according to claim 12, wherein said anchoring results with said narrowing being shaped to cover an entire cross section of a blood vessel lumen occupied by said implant body, thereby completely blocking blood flow therethrough when said space is filled with said tissue ingrowth sufficiently to block said blood flow from passing across said narrowing.

15. The method according to claim 12, wherein said implant comprises a tubular implant body having an implant proximal portion, an implant distal portion, and an implant intermediate portion provided between said implant proximal and distal portions, and wherein said implant intermediate portion is shaped with a narrowing and comprises a plurality of openings for allowing blood flow passage across said narrowing.

16. The method according to claim 15, wherein said proximal implant portion descends in diameter in a proximal-to-distal direction and/or said distal implant portion ascends in diameter in a proximal-to-distal direction.

17. The method according to claim 12, wherein said implant body includes a tubular inner layer forming said narrowing, and a tubular outer layer provided coaxially around said inner layer and configured for anchoring the implant to said target wall portion.

18. The method according to claim 17, wherein the disintegrating is performed by rotating the outer layer against the blood vessel.

19. The method according to claim 17, wherein said inner layer is formed of a first material provided in a plastically deformable state for facilitating selective radial changeability in diameter of said narrowing between a plurality of fixed diameters.

20. The method according to claim 17, wherein said inner layer is formed of a first material provided in an elastically deformable state for facilitating self-expansion from a predetermined initial orifice diameter to said final orifice diameter of said orifice.

21. The method according to claim 17, wherein said inner layer and/or said outer layer includes a mesh, a wire, peripheral slits or struts.

22. The method according to claim 12, wherein said inducing further comprises providing a tissue growth inducing agent in or around said space.

23. The method according to claim 22, wherein said tissue growth inducing agent comprises growth factors.

* * * * *